(12) United States Patent
Fan et al.

(10) Patent No.: US 8,187,187 B2
(45) Date of Patent: May 29, 2012

(54) SHEAR WAVE IMAGING

(75) Inventors: Liexiang Fan, Sammamish, WA (US);
Paul Freiburger, Seattle, WA (US);
Richard Chiao, Cupertino, CA (US);
Greg Sherwin, Renton, WA (US);
Thomas Edward Cezeaux, New Castle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 817 days.

(21) Appl. No.: 12/174,011

(22) Filed: Jul. 16, 2008

(65) Prior Publication Data

US 2010/0016718 A1 Jan. 21, 2010

(51) Int. Cl.
*A61B 8/00* (2006.01)

(52) U.S. Cl. .......................................... 600/438

(58) Field of Classification Search .......... 600/437–438, 600/443–447, 462–463
See application file for complete search history.

(56) References Cited

U.S. PATENT DOCUMENTS

| | | | |
|---|---|---|---|
| 5,107,837 A | 4/1992 | Ophir et al. | |
| 5,178,147 A | 1/1993 | Ophir et al. | |
| 5,293,870 A | 3/1994 | Ophir et al. | |
| 5,810,731 A | 9/1998 | Sarvazyan et al. | |
| 6,148,095 A * | 11/2000 | Prause et al. | 382/131 |
| 6,278,890 B1 * | 8/2001 | Chassaing et al. | 600/407 |
| 6,508,768 B1 | 1/2003 | Hall et al. | |
| 6,558,324 B1 | 5/2003 | Von Behren et al. | |
| 6,561,981 B2 * | 5/2003 | Bonnefous | 600/443 |
| 6,733,461 B2 * | 5/2004 | Bratteli | 600/490 |
| 6,764,448 B2 | 7/2004 | Trahey et al. | |
| 6,770,033 B1 | 8/2004 | Fink et al. | |
| 6,951,544 B2 | 10/2005 | Trahey et al. | |
| 7,374,538 B2 * | 5/2008 | Nightingale et al. | 600/443 |
| 7,736,314 B2 * | 6/2010 | Beach et al. | 600/437 |
| 7,744,535 B2 * | 6/2010 | Vanderby et al. | 600/438 |
| 7,744,537 B2 * | 6/2010 | Kanai et al. | 600/453 |
| 7,751,984 B2 * | 7/2010 | Tang | 702/19 |
| 7,753,847 B2 * | 7/2010 | Greenleaf et al. | 600/438 |
| 7,930,014 B2 * | 4/2011 | Huennekens et al. | 600/407 |
| 2005/0070798 A1 * | 3/2005 | Pedrizzetti et al. | 600/442 |
| 2005/0252295 A1 | 11/2005 | Fink et al. | |
| 2008/0249408 A1 * | 10/2008 | Palmeri et al. | 600/438 |
| 2009/0216131 A1 * | 8/2009 | Chase et al. | 600/476 |
| 2010/0222678 A1 * | 9/2010 | Bercoff et al. | 600/442 |
| 2010/0280373 A1 * | 11/2010 | Fan et al. | 600/439 |
| 2011/0063950 A1 * | 3/2011 | Greenleaf et al. | 367/87 |

OTHER PUBLICATIONS

U.S. Appl. No. 12/038,683, filed Feb. 27, 2008.
U.S. Appl. No. 12/028,203, filed Feb. 8, 2008.

* cited by examiner

*Primary Examiner* — Francis Jaworski

(57) ABSTRACT

Shear wave imaging is provided in medical diagnostic ultrasound. A region is imaged to determine a location in which to calculate shear velocity. The shear velocity is estimated for the location. The imaging may guide the identification of the location, reducing the time to determine useful shear information. The estimate of shear may be validated, such as using cross-validation, to indicate the confidence level of the shear value. The shear velocity may be displayed relative to a scale of shear velocities associated with a type of tissue, such as tissue for an organ. The location on a scale may be more intuitive for a user.

15 Claims, 2 Drawing Sheets

SHEAR WAVE IMAGING

BACKGROUND

The present embodiments relate to shear wave imaging. Ultrasound may be used to detect a shear wave in tissue.

Shear is a viscoelastic property of tissue. The shear wave velocity of tissue may indicate useful information about the health of the tissue. Shear wave images may be generated. A characteristic of the shear wave in the tissue is determined for different spatial locations. An image of the characteristic as a function of space is generated. However, a large number of transmissions and receptions are used to estimate shear wave information in a large region, resulting in a slow frame rate.

Another tissue property or component of viscoelasticity is elasticity. Ultrasound imaging may operate in an elasticity imaging mode. U.S. Pat. Nos. 5,107,837; 5,293,870; 5,178,147; and 6,508,768 describe methods to generate elasticity images using the relative tissue displacement between adjacent frames. The tissue strain is determined in response to a stress applied to tissue. The stress is applied externally, such as by manual pressure or by acoustic pressure. Strain or strain rate are detected for generating an elasticity image. Altered stiffness regions may be identified. However, strain is relative or qualitative. For example, different amounts of applied stress result in different amounts of strain. The amount of applied stress may be unknown or difficult to determine accurately.

BRIEF SUMMARY

By way of introduction, the preferred embodiments described below include methods, instructions, and systems for shear wave imaging in medical diagnostic ultrasound. A region is imaged to determine a location in which to calculate shear velocity. The shear velocity is estimated for the location. The imaging may guide the identification of the location, reducing the time to determine useful shear information. The estimate of shear may be validated, such as using cross-validation, to indicate the confidence level of the shear value. The shear velocity may be displayed relative to a scale of shear velocities associated with a type of tissue, such as tissue for an organ. The location on a scale may be more intuitive for a user. Any one or combination of two or more features may be used.

In a first aspect, a method is provided for shear wave imaging in medical diagnostic ultrasound. A two or three-dimensional region of a patient is imaged with ultrasound. A location for shear velocity estimation is identified. The location is in the two or three-dimensional region. Shear velocity is estimated at the location.

In a second aspect, a computer readable storage medium has stored therein data representing instructions executable by a programmed processor for shear wave imaging in medical diagnostic ultrasound. The storage medium includes instructions for obtaining ultrasound data, at least some of the ultrasound data responsive to a shear wave, estimating a shear velocity from the ultrasound data, validating the shear velocity as a function of the ultrasound data, and displaying the cross validated shear velocity.

In a third aspect, a system is provided for shear wave imaging in medical diagnostic ultrasound. A processor is operable to estimate a shear velocity. A display device is operable to output a velocity range associated with a type of tissue and indicate the shear velocity within the range.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Shear velocity is estimated. Acquiring shear velocity information rapidly may improve the clinical workflow. The shear velocity estimation is integrated with real-time ultrasound imaging. B-mode, color flow, elasticity, or other imaging is performed to identify one or more locations for which shear velocity may be particularly relevant. For example, elasticity imaging indicates a small region with increased stiffness relative to other regions. A gate or region of interest for shear velocity is placed manually or automatically. Shear velocity is estimated for this region, providing information for the region of interest and limiting delay to acquire shear velocity information over a greater area.

Due to complicated body motion and variation in tissue mechanical property distribution even in a small region of interest, shear velocity or other property may be erroneous or noisy. The shear value may be validated, such as providing a level of confidence associated with the shear value. For example, a data set used to determine shear velocity is divided into subsets. Using the divided subsets, a cross-validation is performed, such as validating with a leave-one-out approach. This confidence level is indicated as a value and/or by selecting whether to display the shear velocity. The user may better rely on validated information.

A shear value alone may provide little information without specific knowledge relating the shear value to diagnosis for different tissue types. Marking the shear value on a map representing a range of values associated with a type of tissue (e.g., organ) may provide information that is more intuitive to the user. The frame of reference may aid in understanding the significance of a given shear value.

Figure 1:
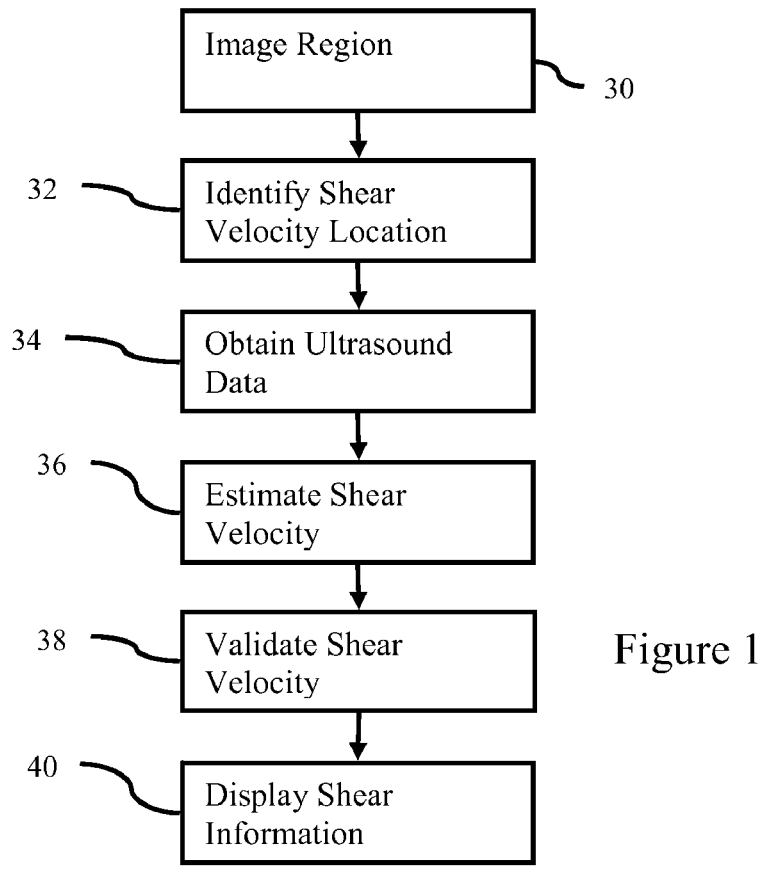
FIG. 1 is a flow chart diagram of one embodiment of a method for shear wave imaging in medical diagnostic ultrasound.

FIG. 1 shows a method for shear wave imaging in medical diagnostic ultrasound. The method is implemented by the system of FIG. 4 or a different system. Additional, different, or fewer acts may be provided. For example, acts for assisting in locating a region to estimate shear, validating shear, or displaying shear are performed alone or in any combination. The acts are performed in the order described or shown, but may be performed in other orders.

In act 30, a region is imaged. The region is a two or three-dimensional region of a patient. For imaging a volume, the data is rendered to a planar presentation or three-dimensional representation on a two-dimensional display. Alternatively, a one-dimensional region is imaged.

Any type of imaging may be used. For example, ultrasound imaging is provided. B-mode, color flow (Doppler velocity, energy, and/or variance), elasticity, acoustic force radiation imaging, harmonic imaging, or other now known or later developed imaging mode is used to generate an image or sequence of images. Combination images using multiple modes may be provided, such as B-mode in combination with one of the other modes. Acoustic force radiation imaging detects displacement of tissue in response to pressure applied to the tissue with acoustic energy.

In elasticity imaging, an external source of pressure is provided. For example, an acoustic radiation force impulse is transmitted with a focal point at or adjacent to a location. Other sources of stress may be used, such as manually or internally generated stress. For example, a user applies pressure axially with a transducer.

The stress may be added or released. The applied stress may be an impulse, cyclical, repeating, or a non-impulse stress. For example, the pressure applied due to breathing or the heart is cyclical. The stress is applied repetitively, or differently as a function of time. The applied stress may be represented by an impulse. A substantially single pressure wave is generated. The impulse may be generated by a cyclical pulsed waveform of any number of cycles (e.g., tens or hundreds of cycles). For example, acoustic radiation force is transmitted as an impulse for applying stress to tissue. The impulse wavefront propagates to the region of interest.

The response of tissue along transmit or receive beams is detected. Doppler or B-mode scanning may be used. Ultrasound imaging is performed before, during and/or after the stress is applied. Ultrasound data is received in response to transmissions of ultrasound. The transmissions and receptions are performed for a single spatial location (e.g., the focal point of the applied stress), along a line, over an area, or over a volume. A sequence of transmissions and receptions are provided for each spatial location.

The displacement of tissue along scan lines is determined as a function of time. The displacement may be measured from tissue data, such as B-mode ultrasound data. Correlation, cross-correlation, minimum sum of absolute differences or other similarity measure is used to determine the displacement between scans. The displacements are determined along one, two, or three dimensions. In one embodiment, any one or more of the methods or systems disclosed in U.S. Pat. Nos. 5,107,837; 5,293,870; 5,178,147; 6,508,768 or 6,558,324, the disclosures of which are incorporated herein by reference, are used to generate elasticity frames of data or images as the strain information. Other methods of measuring strain with or without determining displacement of tissue in response to application or change in stress may be used. The displacement may be measured by determining tissue velocity and/or acceleration.

Based on one (e.g., velocity), two (B-mode correlation), or more (e.g., average displacement) scans, a strain field is determined. The strain field represents strain at the different locations. A displacement field or a strain rate field may be used in other embodiments. Other measurements may be used to represent strain or displacement, such as velocity.

The elasticity image indicates the stiffness of tissue, so may provide an indication of abnormal tissue. B-mode mode images may show a tissue region differently than surrounding tissue, indicating possible abnormal tissue. A color flow image may indicate tissue associated with less movement than expected or other abnormal movement. Other modes of imaging may provide an indication of possible abnormal tissue. A medical professional may have other information indicating a location in the patient associated with a possible abnormality, such as other images (e.g., x-ray, computed tomography, or magnetic resonance images), lab tests, or training.

Figure 2:
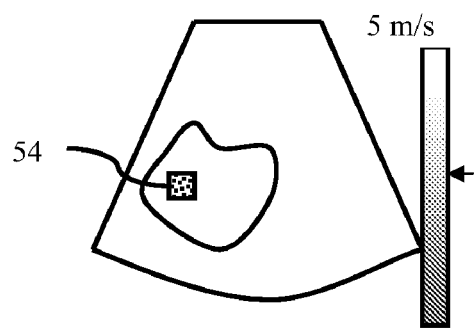
FIG. 2 is an example illustration of an image with shear velocity information.

In act 32, a location for shear velocity estimation is identified. The location is in the two or three-dimensional region that is imaged. The location may be identified independent of the imaging, such as desiring information for a specific part of an organ. In other embodiments, the location is identified in one or more of the images from the imaging of act 30. FIG. 2 shows a two-dimensional sector scan. The image from the scan shows an organ in the scanned region. A location 54 is identified in the organ represented by the image. The imaging of act 30 provides information for identifying a location for which further information is desired, such as identifying a possible abnormal tissue location. Imaging aids the workflow and assists in limiting the area for which shear velocity or other tissue property is to be measured.

The location is a point, line, area, or volume. More than one location may be identified. A region of the patient is imaged, and a region of interest within the region is identified in act 32.

A user identifies the location. The user examines one or more images, such as an ongoing sequence of images displayed as the images are acquired (e.g., in real-time with scanning). The user may examine one or more previously acquired images, such as from CINE memory or image archive. The user enters the location for further study with a user interface. For example, the user navigates a pointer over the image to the location of a possible abnormality, and then clicks or activates the user input to indicate the location.

Alternatively, a processor automatically identifies the location from the ultrasound imaging. Any image processing may be used to identify the location. For example, an image is filtered to isolate a region of interest. As another example, region growing, border detection, or other techniques are used alone or in combination. In one embodiment, an image is segmented. For example, an elasticity image is divided into areas associated with different levels of intensity. A low pass filter may be applied to minimize noise before or after segmentation. A segment is selected as the location. For example, the location corresponding to the brightest, darkest, or mean intensity is selected. For elasticity imaging, the darkest location may indicate the stiffest tissue, so the darkest location is selected. Other segmenting and selecting may be used.

In act 34, ultrasound data is obtained. At least some of the ultrasound data is responsive to a shear wave. A shear wave is generated by focused acoustic energy. For example, acoustic energy is transmitted along a scan line and focused at a point or region adjacent to or within the identified location. The acoustic energy is a single or few pulses for generating a shear wave. The shear wave propagates through tissue more slowly than the longitudinal wave along the acoustic wave emission direction. The shear wave propagates various directions, including a direction perpendicular to the direction of the applied stress.

A region of interest at the location is monitored to detect the shear wave. The region of interest is any size, such as 6 mm in lateral and 10 mm in axial. This region is monitored by ultrasound. For example, B-mode scans are performed to detect tissue displacement caused by the shear wave. Doppler, color flow, or other ultrasound mode may be used to monitor for the shear wave.

The monitoring is performed for any number of scan lines. For example, four receive beams are formed in response to each transmission. After transmitting the acoustic force to generate the shear wave, B-mode transmissions are performed repetitively along a single scan line and receptions along four adjacent scan lines. Any number of repetitions may be used, such as about 120 times. Some of the ultrasound data, such as at the beginning or end of the repetitions, may not be responsive to the shear wave. In other embodiments, only a single receive beam or other numbers of receive beams are formed in response to each transmission.

As the shear wave propagates through the scan lines, the B-mode intensity may vary. For the monitored scan lines, a sequence of data is provided representing a time profile of tissue motion resulting from the shear wave. For example, data from a plurality of spatial locations (e.g., along the scan lines) is correlated as a function of time. Any elasticity detection may be used. For each depth or spatial location, a correlation over a plurality of depths or spatial locations (e.g., kernel of 64 depths with the center depth being the point for which the profile is calculated) is performed. The spatial offset with the highest or sufficient correlation at a given time indicates the amount of displacement. The displacement is determined between times for the different depths. For each location, the displacement as a function of time is determined. Two or three-dimensional displacement in space may be used. One-dimensional displacement along a direction different than the scan lines or beams may be used.

To monitor a larger region, additional receive beams are formed in response to the monitoring transmit beam. Alternatively, another shear wave is generated and the transmit beams and receive beams are provided at a different distance from the shear wave generation point. In the 6 mm×10 mm example above, 36 receive scan lines may be provided. At four receive beams per transmit beam, the process is repeated for different lateral spacing nine times. For each receive beam location, a time profile of motion information is provided, represented by the ultrasound data. Transmissions along different scan lines to monitor a same shear wave are avoided during formation of the temporal profile to provide higher temporal resolution, but interleaved or shifting scanning positions may be provided.

The discussion above is for one depth. The sampling may be arranged to provide one gate covering the entire axial extent of the region of interest. In another embodiment, samples are obtained at multiple depths for each receive beam. A separate time profile is provided for each axial depth as well as lateral location. Any number of depths may be used, such as about 200 for 5 mm or 400 for 10 mm.

Ultrasound data representing different locations in the region of interest is obtained. The ultrasound data is obtained in real-time with the scanning or obtained from a memory. For each location, the motion information represents the response at different times, providing a temporal profile. Other scanning, monitoring, or techniques may be used to obtain ultrasound data to estimate shear velocity.

In act 36, shear velocity at the location is estimated. Other tissue properties may be estimated. The shear velocity is estimated from the ultrasound data obtained in act 34. The shear velocity is obtained by determining a time from generation of the shear wave until detection of the shear wave at a different location. The time and distance to the location determine the velocity. The distance is known from the scan line spacing (i.e., the transmit beam position for generating the shear wave and the receive beam position for detecting the shear wave). The time is known from the relative time between generation and detection of the shear wave.

Figure 3:
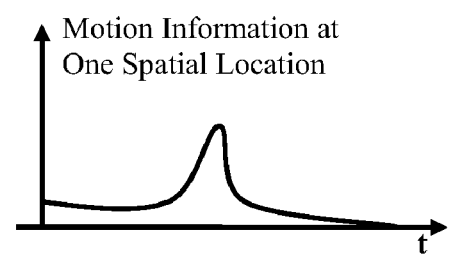
FIG. 3 is an example graphical representation of a time profile of tissue motion information, such as displacements, as a function of time at a location responsive to a shear wave.

The temporal profile for a given location indicates detection of the shear wave. FIG. 3 shows an example temporal profile. The profile is examined for a non-noise or single instance of variation. A peak in the profile, with or without temporal low pass filtering, indicates the passing of the shear wave front.

Other techniques may be used to detect the peak in the profile. For example, a regression is applied. Since the shear wave velocity is linear, a robust linear regression with automated outlier detection may indicate the shear wave velocity. The ultrasound data for all of the sample points in the region of interest is plotted for distance as a function of time or by time and distance. The linear regression is applied to the plot or data, providing a line fit to the data. The slope of the line indicates the shear wave velocity.

Other approaches may be used. For example, data from different times is correlated to detect the shift in tissue caused by the shear wave. As another example, a feature is extracted from the temporal profiles. Principle component decomposition may be used. A correlation between the different temporal profiles is performed. The lag associated with the different distances for the different temporal profiles provides the velocity. Alternatively, a wavelet analysis may be performed. A wavelet transform is applied to the temporal profiles to identify a peak corresponding to the shear wave. A velocity value is identified from the travel time of the peak to each spatial location.

All the peak travel time data from the full region of interest may be used together, such as in linear regression. Only a subset of the data may be used, such as using data for one depth for feature extraction or regression. A single shear velocity is calculated. A plurality of shear velocities may be calculated for the region of interest. The results may be averaged or otherwise combined. For example, linear regression is applied to ten or other number of subsets. Each subset includes data for different depth ranges, such as each subset including data for twenty different depths. Shear velocity is determined for each subset. The average shear velocity is used. A variance or other statistical information may be derived from the different shear velocities. Alternatively, a spatial representation of shear wave velocity variance within the region of interest may be provided.

In act 38, the shear velocity is validated. The shear velocity may be validated using the ultrasound data also used to estimate the shear velocity. For example, cross validation is used. A leave-one-out cross validation may indicate the confidence level for the estimated velocity. In one embodiment, the ultrasound data is grouped into subsets. Any number of groups may be provided, such as ten subsets. The data to be included in a given group may be by location, such as each subset being associated with different depths and/or lateral locations. The shear velocity is estimated from different groupings of subsets, such as determining nine shear velocity estimates each associated with leaving a different one of the ten subsets out. The variance or correlation of the shear velocities indicates a confidence level. A lower variance or higher correlation indicates higher confidence. The distribution of shear velocities may indicate confidence, such as most or a higher percentage of the estimated shear velocities having similar values despite a few having very different values.

For example, a cross-validation method is applied by leaving out a subset data of one depth. All peak travel time data except in one depth are used in linear regression to generate one shear velocity. This shear value is then used in a correlation coefficient computation for the excluded depth data to give a confidence level. This method is applied to each depth to derive confidence levels at ten or more or fewer depths. The confidence levels are ranked from high to low, and the data sets with confidence level above certain predefined threshold, e.g. 75%, are used together to generate a final shear velocity.

In another example of validation from the ultrasound data, the confidence level is determined as a function of the error in the estimating. For example, an error is provided as part of the linear regression. The error represents the variation in the data. A higher error may indicate a less reliable shear velocity estimate. Other validation using the data may be used.

If the shear velocity is sufficiently valid, then the shear velocity information is provided to the user or output. Alternatively or additionally, a confidence level is output with the shear velocity.

In act 40, shear information is displayed. Any shear information may be displayed. For example, the shear velocity is displayed. FIG. 2 shows a shear velocity value of 1.41 m/s displayed adjacent an image. The shear velocity is for the region of interest 54. The velocity may be displayed on the image or without the image. A representation of shear velocity may be used instead of an actual number, such as mapping a color or otherwise modulating the pixels at the region of interest 54 as a function of the shear velocity. For example, a high velocity is mapped to a brighter red than a lower velocity.

The shear velocity may be indicated relative to a range of shear velocities with or without other shear velocity information. For example, a bar, line, graph or other representation of a range of shear velocities is displayed. The range may be for tissue or may be specific to type of tissue. For example, the user inputs or a processor identifies the type of tissue for which velocity is measured. A range of normal and abnormal velocities for that type of tissue is output. The range does or does not indicate normal or abnormal velocities. The estimated shear velocity is shown on the range, such as an arrow or other indicator of the estimated shear velocity range. The relative position may be more intuitive to a user.

The shear velocity may be validated. An indication of the validation may be output. For a binary indication, outputting the shear velocity indicates validation. A confidence level, percentage, error, or other validation information may be output with the shear velocity. For example, a confidence level tag or text is output with the shear velocity.

The shear information may include an indication of the location. FIG. 2 shows an example where an indication marker shows the region of interest 54 for which shear velocity is estimated. The marker is on an image representing the scanned region. The image may assist the user in understanding the relative anatomy and/or provide further information about the region of interest or state of tissue. The image may be static or may be continuously updated for real-time imaging.

Figure 4:
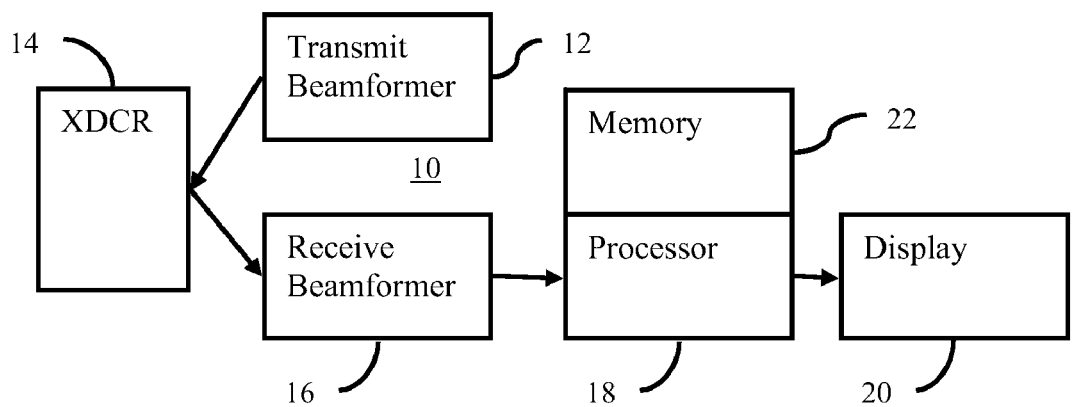
FIG. 4 is a block diagram of one embodiment of a system for shear wave imaging in medical diagnostic ultrasound.

FIG. 4 shows one embodiment of a system 10 for shear wave imaging in medical diagnostic ultrasound. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted selection of display maps, tissue properties to be determined, region of interest selection, or other control. The system 10 is a medical diagnostic ultrasound imaging system. In alternative embodiments, the system 10 is a personal computer, workstation, PACS station, or other arrangement at a same location or distributed over a network for real-time or post acquisition imaging, so may not include the beamformers 12, 16 and transducer 14.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed. A sequence of transmit beams are generated to scan a two or three-dimensional region. Sector, Vector®, linear, or other scan formats may be used. The same region is scanned multiple times. For flow or Doppler imaging and for strain imaging, a sequence of scans are used. In Doppler imaging and shear velocity estimation, the sequence may include multiple beams along a same scan line before scanning an adjacent scan line. For strain imaging, scan or frame interleaving may be used (i.e., scan the entire region before scanning again). In alternative embodiments, the transmit beamformer 12 generates a plane wave or diverging wave for more rapid scanning.

The transmit beams are formed at different energy or amplitude levels. Amplifiers for each channel and/or aperture size control the amplitude of the transmitted beam. Transmit beams to generate a shear wave and/or for strain imaging may have greater amplitudes than for imaging or monitoring for the shear wave.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to a transmission. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for shear wave velocity estimation. Data received for B-mode or other imaging may be used for estimation of shear velocity.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, network, server, group of processors, data path, combinations thereof or other now known or later developed device for detecting and processing information for display from beamformed ultrasound samples. In one embodiment, the processor 18 includes one or more detectors and a separate processor. The processor 18 is operable to estimate shear wave velocity, validate the estimate, and/or coordinate display of information. For example, the processor 18 performs any combination of one or more of the acts shown in FIG. 1.

The processor 18 estimates shear velocity by detecting a time for the shear wave to travel a distance. Multiple estimates may be provided and/or data from different locations used for one estimate. Linear regression, correlation, principle component extraction, wavelet transforms, or other estimation techniques may be used. Any or no validation of the estimate may be performed by the processor 18.

In one embodiment, the processor 18 implements a classifier. Through programming or machine learning, the classifier distinguishes between diseased and non-diseased tissue. The classifier is specific to a type of tissue, accounts for the type of tissue, or is generic to the type of tissue. The classifier scores the disease level based, at least in part, on the shear velocity. Any score system may be used, such as a single threshold. If the velocity is above or below the threshold for a given type of tissue, then the tissue is diseased. More complex scoring may be used, such as associated with clinical studies distinguishing between stages or types of disease based, at least in part, on the shear velocity. The score (e.g., level 1-5) may be output.

The processor 18 generates display data, such as graphic overlays and images. The display data is in any format, such as values before mapping, gray scale or color-mapped values, red-green-blue (RGB) values, scan format data, display or Cartesian coordinate format data, or other data. The processor 18 outputs data appropriate for the display device 20.

The processor 18 operates pursuant to instructions stored in the memory 22 or another memory. The processor 18 is programmed for shear wave imaging in medical diagnostic ultrasound. The memory 22 is a computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display device 20 is a CRT, LCD, projector, plasma, printer, or other display for displaying shear velocity, graphics, user interface, validation indication, two-dimensional images, or three-dimensional representations. The display device 20 displays ultrasound images, the shear velocity, and/or other information. The displayed information is in a report or screen presentation.

The display device 20 is operable to output a velocity range associated with a type of tissue and indicate the estimated shear velocity within the range. The display device 20 receives the graphics information for this output from the processor 18. The display device 20 generates a visual representation of the graphic, such as the bar or other range scale. An indication of the estimated shear velocity relative to the range is also generated, such as generating an arrow, color, bar, text, or other graphic adjacent to, overlaid on, combined with, or associated with the range.

The display device 20 outputs an image of a region of the patient, such as a two-dimensional elasticity, Doppler tissue, or B-mode image. The image includes a location indicator for the shear velocity. The location relative to the imaged tissue for which shear velocity is calculated is shown. The shear velocity is provided on or adjacent the image of the region.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for shear wave imaging in medical diagnostic ultrasound, the method comprising:
    ultrasound imaging a two or three-dimensional region of a patient;
    identifying a location for shear velocity estimation from the ultrasound imaging, the location in the two or three-dimensional region;
    estimating, with a processor, shear velocity at the location;
    displaying a location marker on an image of the ultrasound imaging, the location marker being at the location; and
    displaying the shear velocity on said image for the said location on the image.

2. The method of claim 1 wherein ultrasound imaging comprises B-mode, color flow, elasticity, or acoustic force radiation imaging.

3. The method of claim 1 wherein ultrasound imaging comprises generating a first image, and wherein identifying the location comprises identifying the location in the first image.

4. The method of claim 1 wherein identifying comprises a user identifying from the ultrasound imaging and entering the location with a user interface.

5. The method of claim 1 wherein identifying comprises automatically identifying with the processor from the ultrasound imaging.

6. The method of claim 5 wherein automatically identifying comprises segmenting an image and selecting a segment.

7. In a non-transitory computer readable storage medium having stored therein data representing instructions executable by a programmed processor for shear wave imaging in medical diagnostic ultrasound, the storage medium comprising instructions for: three-dimensional region of a patient;
    obtaining ultrasound data, at least some of the ultrasound data responsive to a shear wave; velocity estimation from the ultrasound imaging, the location in the two or three-dimensional region;
    estimating a shear velocity at the location from the ultrasound data;
    validating the shear velocity as a function of the ultrasound data; and
    displaying the validated shear velocity on said image for the said location.

8. The non-transitory computer readable storage medium of claim 7 wherein obtaining the ultrasound data comprises obtaining data representing different locations, the ultrasound data for each location including data at different times.

9. The non-transitory computer readable storage medium of claim 8 wherein the ultrasound data for each location comprises a temporal profile, and wherein estimating the shear velocity comprises extracting a feature from the temporal profile by principle component decomposition or wavelet analysis and processing the feature.

10. The non-transitory computer readable storage medium of claim 7 wherein estimating the shear velocity comprises applying linear regression to the ultrasound data plotted for distance as a function of time.

11. The non-transitory computer readable storage medium of claim 7 wherein validating comprises grouping the ultrasound data in to a plurality of subsets by location and cross validating with a leave one out approach.

12. The non-transitory computer readable storage medium of claim 11 wherein estimating comprises estimating from a full set of the ultrasound data, and wherein cross validating comprises determining whether the shear velocity is valid as a function of velocities determined with the leave one out approach.

13. The non-transitory computer readable medium of claim 7 wherein validating comprises determining a confidence level as a function of an error in the estimating.

14. A system for shear wave imaging in medical diagnostic ultrasound, the system comprising:
    a processor operable to estimate a shear velocity; and
    a display device operable to output a graphic representation of a velocity range associated with a type of tissue and indicate on the graphic representation the shear velocity within the range being operable to score a disease level as a function of the shear velocity and the velocity range for the type of tissue, and said display device being operable to output the score, said display device being further operable to display an image of a region of a patient, the image including a location indicator for the shear velocity, and said score being displayed in association with said location indicator.

15. The system of claim 14 wherein the velocity range is a bar and the indication of the shear velocity is relative to the bar.

* * * * *